US009752699B2

(12) United States Patent
Holder

(10) Patent No.: US 9,752,699 B2
(45) Date of Patent: Sep. 5, 2017

(54) GAS CONSERVING DEVICE

(75) Inventor: Gary N Holder, Ringgold, GA (US)

(73) Assignee: RIC INVESTMENTS, LLC, Wilmington, DE (US)

( * ) Notice: Subject to any disclaimer, the term of this patent is extended or adjusted under 35 U.S.C. 154(b) by 2509 days.

(21) Appl. No.: 12/105,309

(22) Filed: Apr. 18, 2008

(65) Prior Publication Data

US 2008/0236584 A1    Oct. 2, 2008

Related U.S. Application Data

(62) Division of application No. 11/096,993, filed on Apr. 1, 2005, now Pat. No. 7,370,651.

(51) Int. Cl.
*A61M 16/06* (2006.01)
*F16K 31/06* (2006.01)
*A61M 16/00* (2006.01)
*A62B 7/04* (2006.01)

(52) U.S. Cl.
CPC ..... *F16K 31/0627* (2013.01); *A61M 16/0666* (2013.01); *A61M 16/0672* (2014.02); *A61M 16/0677* (2014.02); *A61M 2016/0021* (2013.01); *A61M 2016/0027* (2013.01); *A62B 7/04* (2013.01)

(58) Field of Classification Search
CPC .... A61M 2016/101; A61M 2205/8212; A61M 2016/0677; A61M 16/20; A61M 16/0666; A61M 16/0672; A62B 7/04
USPC ........... 128/204.18, 204.19, 204.21, 204.23, 128/204.26, 205.24; 244/118.5; 137/487.5, 624.11
See application file for complete search history.

(56) References Cited

U.S. PATENT DOCUMENTS

| 3,188,836 | A | * | 6/1965 | Kniebes | ................... 431/18 |
| 3,330,133 | A | * | 7/1967 | Kniebes | ................... 431/60 |
| 3,424,426 | A | * | 1/1969 | Neff | ................... 251/30.03 |
| 3,726,274 | A | | 4/1973 | Bird et al. | |

(Continued)

OTHER PUBLICATIONS

"Magnetic Properties of Stainless Steels", Carpenter Technical Articles, Jun. 2006 http://www.cartech.com/techarticles.aspx?id=1476.*

(Continued)

*Primary Examiner* — Justine Yu
*Assistant Examiner* — LaToya M Louis
(74) *Attorney, Agent, or Firm* — Michael W. Haas

(57) ABSTRACT

An electronic oxygen conserving device for controlling a flow of oxygen from an oxygen storage container to a user. When a conserve setting is selected, a flow of oxygen travels through an oxygen regulating valve that has an open state and a closed state. A temporary electrical charge or current is provided to the oxygen regulating valve during the initial inhalation of oxygen by an individual, opening the regulating valve opens to delivery oxygen to the user. The oxygen regulating valve remains open even after termination of the electric current. After a predetermined timed delivery dose or upon exhalation by the individual, a subsequent temporary electric charge or current is provided to oxygen regulating valve, closing the regulating valve closes to prevent delivery of oxygen to the user, thus conserving oxygen. The oxygen regulating valve remains closed even after termination of the subsequent electric current.

8 Claims, 4 Drawing Sheets

(56) References Cited

U.S. PATENT DOCUMENTS

| | | | |
|---|---|---|---|
| 3,731,670 A * | 5/1973 | Loe | 600/30 |
| 4,345,592 A | 8/1982 | Giorgini et al. | |
| 4,482,346 A * | 11/1984 | Reinicke | 604/152 |
| 4,519,387 A | 5/1985 | Durkan et al. | |
| 4,686,975 A | 8/1987 | Naimon et al. | |
| 4,714,234 A * | 12/1987 | Falk et al. | 251/129.17 |
| 4,967,996 A * | 11/1990 | Sonoda et al. | 251/30.02 |
| 5,099,837 A | 3/1992 | Russel, Sr. et al. | |
| 5,165,397 A | 11/1992 | Arp | |
| 5,180,138 A * | 1/1993 | Moldenhauer | 251/30.05 |
| 5,593,134 A * | 1/1997 | Steber et al. | 251/129.17 |
| 5,603,315 A | 2/1997 | Sasso, Jr. | |
| 5,735,268 A | 4/1998 | Chua et al. | |
| 5,881,725 A | 3/1999 | Hoffman et al. | |
| 5,893,275 A | 4/1999 | Henry | |
| 5,928,189 A | 7/1999 | Phillips et al. | |
| 6,148,816 A * | 11/2000 | Heinonen et al. | 128/205.24 |
| 6,152,134 A | 11/2000 | Webber et al. | |
| 6,347,630 B1 | 2/2002 | Takahashi et al. | |
| 6,364,161 B1 | 4/2002 | Pryor | |
| 6,378,520 B1 | 4/2002 | Davenport | |
| 6,394,088 B1 | 5/2002 | Frye et al. | |
| 6,484,721 B1 | 11/2002 | Bliss | |
| 6,776,180 B1 * | 8/2004 | Yonnet | 137/14 |
| 7,150,280 B2 | 12/2006 | Aylsworth et al. | |
| 2004/0194829 A1 * | 10/2004 | Zaiser et al. | 137/544 |
| 2006/0011199 A1 * | 1/2006 | Rashad et al. | 128/204.23 |

OTHER PUBLICATIONS

CHAD Therapeutics, "CHAD Receives FDA Clearance on SAGE™ Oxygen Therapeutic Device", Jun. 16, 2004, http://chadtherapeutics.com/sage.htm.

Marotta, "Miniature Latching High Pressure Valve 2,000psia—Marotta MV602L", Jun. 16, 2004, http://www.marotta.com/DataSheets/MV602L.htm.

The Lee Co., "Lee Presents Latcing Type High Density Interface (HDI), 0.3" centers, to 15 psi, Jun. 16, 2004, http://theleeco.com/EFSWEB2.NSF . . . .

* cited by examiner

GAS CONSERVING DEVICE

CROSS-REFERENCE TO RELATED APPLICATIONS

This application is a Divisional under 35 U.S.C. §120 of U.S. patent application Ser. No. 11/096,993, filed Apr. 1, 2005, now U.S. Pat. No. 7,370,651, the contents of which are incorporated herein by reference.

BACKGROUND OF THE INVENTION

1. Field of the Invention

This invention relates to respiratory gas delivery devices, and, more particularly, to a gas conserving device that utilizes an electronically controlled latching valve to regulate the flow of gas to a user.

2. Description of the Related Art

It is well known to deliver a flow of respiratory gas to a user in the form of supplemental oxygen. The delivery of supplemental oxygen to a patient is typically prescribed for individuals suffering from pulmonary/respiratory problems. The prescription and delivery of supplemental oxygen is undertaken to ensure that sufficient oxygen levels are being received by the patient. Situations in which supplemental oxygen may be prescribed include individual suffers from chronic obstructive pulmonary disease (COPD), asthma, diseased or damaged lungs.

The delivery of supplemental oxygen may be provided utilizing one of three predominant methods. For non-ambulatory patients, or for use during the non-ambulatory period of an individual, oxygen may be provided from a stationary oxygen concentrator that generate oxygen from air, typically using a pressure swing absorption gas separation system. While suitable for their intended purpose, oxygen concentrators are generally ill-suited for portability due the relatively bulky gas compressor and sieve beds needed to generate a practical quantity of oxygen, and, therefore, are not intended for use with an ambulatory individual.

A second predominant oxygen delivery method is a compressed oxygen system in which the oxygen to be consumed by the user is compressed and stored in a high pressure storage vessel or tank. These storage vessels can be made small enough so as to be portable. Compressed gas storage systems are generally prescribed when the user does not need oxygen all the time, such as only when walking or performing physical activity. One disadvantage of compressed oxygen systems is that oxygen is stored under pressure may create a hazard if the storage vessel is damaged, which can occur if it is dropped, bumped, punctured, etc. Also, small, portable oxygen tanks hold a relatively small amount of gas. Thus, they are limited in how long the oxygen inside the tank will last depending on the prescribed flow rate and the type/size of the tank.

A third predominant oxygen delivery method, which is typically used as an alternative to compressed oxygen systems, is a liquid oxygen ("LOX") system. A LOX system includes a large stationary LOX storage canister that stays in the user's home. The stationary LOX canister is replenished periodically from a mobile LOX storage vessels, which is typically a truck carrying a large quantity of LOX. The LOX system also includes a small, portable delivery apparatus weighing from five to thirteen pounds that can be filled from the stationary unit for trips outside the home. The portable delivery apparatus converts the liquid oxygen to a breathable gas for consumption by the user. These systems have limited utilization due to the low LOX capacity of the portable delivery apparatus and the administered LOX flow rate. Furthermore, even when not in use, the LOX within the portable delivery apparatus evaporates at a typical rate of one pound per day, emptying the portable delivery apparatus LOX supply over time even if it is not used. Consequently, a disadvantage of a portable LOX system includes the requirement that the user must return home regularly, such as by the end of the day, to refill the portable delivery apparatus from the home stationary LOX storing canister.

A limiting factor in the utilization of compressed gas and LOX is the small quantity of oxygen stored by these respective systems. In order to ensure the portability of these systems, they tend to be as small as possible, hence limiting the oxygen capacity available for therapeutic utilization. Accordingly, to ensure that the oxygen lasts as long as possible, oxygen conserving devices are typically used in conjunction with these devices. A typical oxygen conserving device controls the delivery of oxygen such that oxygen is delivered to the user during inhalation and terminates during exhalation, i.e., upon detection of cessation of inhalation.

Oxygen conservers typically include a valve for regulating the flow of oxygen to the patient. The control of these valves may either be done electrically or pneumatically. Electrical oxygen conserving devices utilize an electric current to maintain the valve open. A traditional electrical oxygen conserving device utilizes the electric current during the entire inhalation phase of a patient. Accordingly, one of the major drawbacks of an electrical oxygen conserving device is that the power supply, namely the battery or batteries, runs down relatively quickly, necessitating frequent changing of the batteries and constant monitoring of the battery charge. For patients that are elderly or infirm, this maintenance requirement is difficult, if not impossible, and/or burdensome.

U.S. Pat. No. 5,928,189 illustrates an alternative to the traditional electrical oxygen conserving device. This patent illustrates a device including an oxygen valve having a coil that is energized with an electric pulse of a first polarity to open the valve and a subsequent electric pulse of a second polarity to close the valve. The valve is maintained in the open position by residual magnetic flux present in the magnetic circuit. The valve includes a pole piece and plunger, which are simultaneously magnetized by the electric current passing through the coil. While suitable for its intended purpose, this design has two drawbacks. First, the valve remains open only as long as there is a residual magnetic flux in the coil. Consequently, as time passes after the current is terminated, the residual magnetic flux dissipates, removing any magnetic attraction between the pole piece and plunger subjecting the valve to close due to a spring bias. Thus, the duration which the valve may be maintained in an open position is fixed depending upon the current charge provided. An additional drawback to this design is that the circuitry requires a continuous current to be supplied to the control logic, which undesirably limits the useful life of a power source.

Pneumatic oxygen conserving devices do not utilize a power source for manipulating a valve for delivering oxygen, but utilize a dual diaphragm system. A typical prior art pneumatic oxygen conserving device is disclosed in U.S. Pat. No. 6,484,721. In the device taught by this patent, a primary diaphragm controls the flow of oxygen from an oxygen source to a patient. The primary diaphragm has an open position enabling the oxygen to flow and a closed position preventing the oxygen to flow. A second, or master diaphragm, is utilized for relieving pneumatic pressure on the primary diaphragm. This is accomplished by the negative pressure caused by the patient inhaling directly or indirectly moving the slave diaphragm, which results in the pneumatic pressure being released on the primary diaphragm.

A primary drawback of a typical pneumatic oxygen conserving device is the sensitivity of the master diaphragm to an individual's inhalation pressure. If the inhalation pressure produced the patient is too small, the master diaphragm will not respond, and no oxygen will be provided to the patient during that inspiratory cycle. This situation is most likely to occur with patients having diminished respiratory effort, such an elderly patient. Likewise, there may be a time delay between the initial inhalation of the patient and the operation of the pneumatic system before oxygen is permitted to flow to the patient. These drawbacks are the result of a purely mechanical system for controlling the flow of oxygen. Furthermore, by a requiring dual diaphragm construction, multiple components are required. This results in a complex interaction of the components, which may jeopardize the reliability of the conservation device. Also, the addition components may result in a bulky and costly device. Additionally, when rating the utilization of electronic versus pneumatic controllers, electronic controllers generally provide better oxygen conservation results than pneumatic controllers.

There is a need for an oxygen conserving device that operates quickly for the delivery of oxygen to a patient and reliably. There is also a need for an oxygen conserving device that utilizes an electronic control system functioning in a way such that the longevity of its power source is extended, and provides various rates of flows of gas to the patient depending upon the patient's needs.

SUMMARY OF THE INVENTION

Accordingly, it is an object of the present invention to provide an electronic oxygen conserving device that overcomes the shortcomings of conventional oxygen conservers. This object is achieved according to one embodiment of the present invention by providing an electronic oxygen conserving device that includes a valve body having a valve seat disposed in the valve body, and a valve element disposed within the valve body. A portion of the valve element seats against the valve seat when the valve element is in a closed position, and is spaced apart from the seat when to the valve element is in an open position. A permanent magnet is disposed in the valve body and is adapted to magnetically engage the valve element when the valve element is in the open position to maintain the valve element in the open position. An energy source delivers a first energy to the valve element, the permanent magnet, or both to move the valve element to the open position. The energy source also delivers a second energy to valve element, the permanent magnet, or both to move the valve element to the closed position. A sensor monitors a characteristic of a user indicative of respiration. The electronic oxygen conserving device includes a gas flow controller having a plurality of gas flow delivery settings corresponding to a plurality of predetermined gas flow rates/volumes. Finally, a controller controls the energy source based on the gas flow delivery setting and an output of the sensor.

In a second embodiment, this object is achieved by providing a gas conserving device that includes a breath sensor adapted to detect inhalation by a patient, a slave valve, and a pilot valve. The slave valve has an open position for providing a flow of gas from a gas source to a patient, and a closed position for ceasing the flow of gas to the patient. The pilot valve communicates with the slave valve to control a position of the slave valve. An energy source provides a first energy to the pilot valve when to the breath sensor sensing detects inhalation by such a patient. As a result, the pilot valve causes the slave valve to the open position when the slave valve receiving the first energy from the energy source.

The present invention provides a gas conserving device that operates at a very lower power. For example, the present invention uses 5.85E-06 Watts-seconds or less do deliver twelve milliliters or more of or oxygen during a single breath or pulse dose. This power requirement is independent of the volume of oxygen delivered during that breath of pulse dose, the time that the valve is open to deliver the dose of oxygen, or the flow setting selected by the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an" and "the" include plural referents unless the context clearly dictates otherwise.

DETAILED DESCRIPTION OF THE EXEMPLARY EMBODIMENTS

Figure 1:
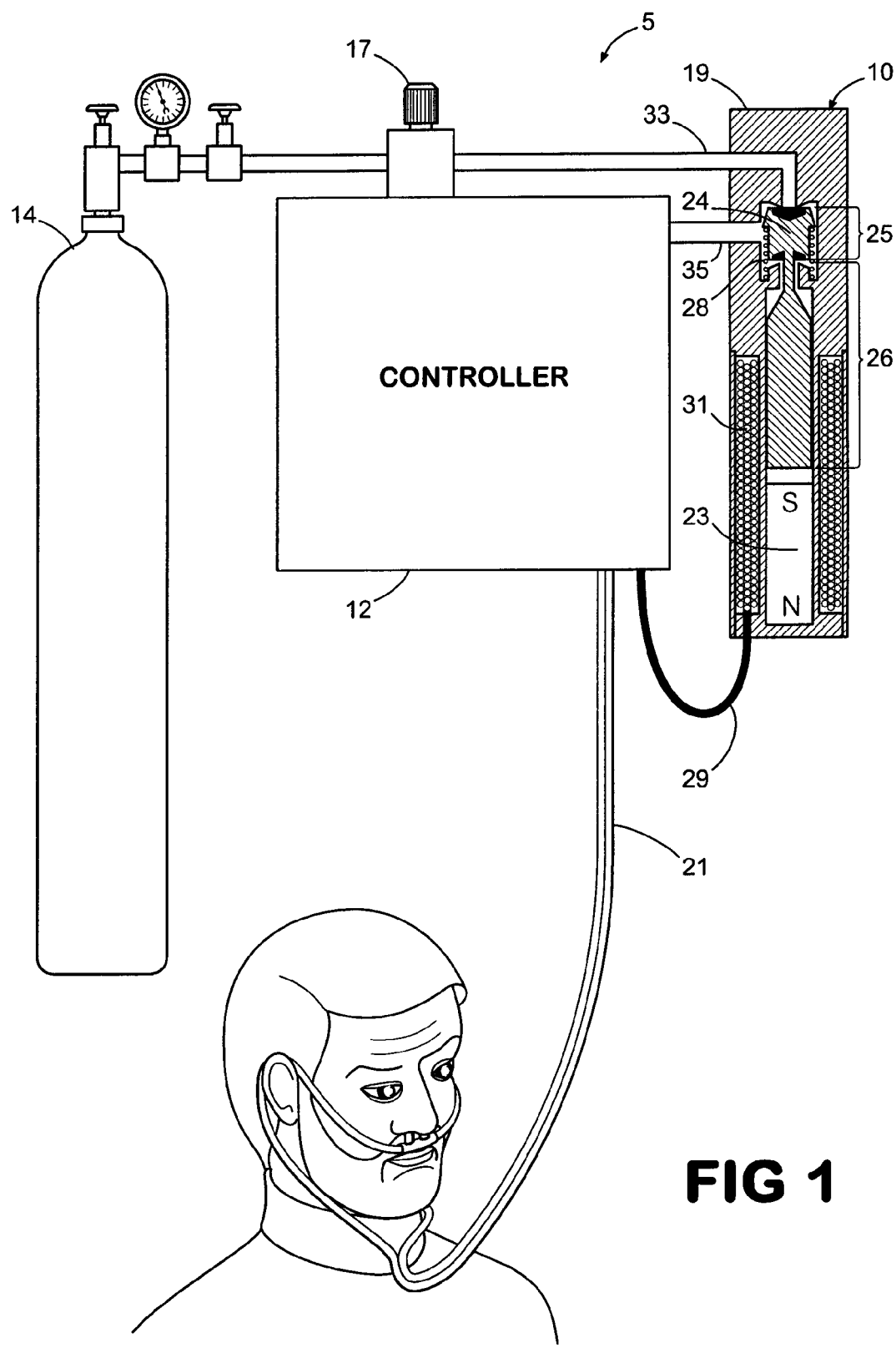
FIG. 1 illustrates an electronic oxygen conserving device according to the principles of the present invention.

Referring now to the drawings, in which like numerals represent like components or steps throughout the several views, FIG. 1 illustrates an electronic oxygen conserving device 5 according to an embodiment of the present invention. Electronic oxygen conserving device 5 is for an individual to use in combination with an oxygen storage container 14 and includes an oxygen conserving controller 12 and an oxygen regulating valve 10. In operation, oxygen storage container 14 provides oxygen to oxygen conserving controller 12, which includes a plurality of oxygen flow settings, e.g., a continuous oxygen flow setting and a conserving (pulse) oxygen flow setting. When oxygen conserving controller 12 is set to the conserving (pulse) oxygen flow setting, the flow of oxygen is provided from oxygen conserving controller 12 to oxygen regulating valve 10 and, subsequently, to a nasal cannula 21. It is to be understood that any conventional oxygen delivery patient interface, such as a mask, can be used in place of or in combination with the nasal cannula.

Oxygen regulating valve 10 opens for a predetermined period of time to allow oxygen to flow freely to from the oxygen storage containing to nasal cannula 21. When an appropriate amount of oxygen has been provided to an individual through nasal cannula 21, oxygen regulating valve 10 is closed to conserve oxygen. More particularly, oxygen conserving controller 12 senses negative pressure from nasal cannula 21 as an individual being the inspiratory phase of the respiratory cycle. Oxygen conserving controller 12 then triggers oxygen regulating valve 10 to an open position to allow oxygen to flow to nasal cannula 21 for a predetermined period of time, e.g., for a period of time related to the oxygen flow setting of oxygen conserving controller 12. Once the predetermined period of time has elapsed or, for example, when oxygen conserving controller 12 senses positive pressure from nasal cannula 21 as the user begins the expiratory phase of the respiratory cycle, oxygen conserving controller 12 triggers oxygen regulating valve 10 to a closed position to prevent oxygen from entering nasal cannula 21, thereby conserving oxygen.

Oxygen storage container 14 communicates with oxygen conserving controller 12 and is adapted to provide a flow of oxygen to oxygen conserving controller 12. Generally, oxygen storage container 14 is initially charged with oxygen from an oxygen supplier or other oxygen storage container. Accordingly, oxygen storage container 14 includes a fill port (not shown) adapted to receive oxygen from an outside source. Oxygen storage container 14 also includes a discharge port (not shown) adapted to provide oxygen from oxygen storage container 14 to oxygen conserving controller 12. One skilled in the art will recognize that oxygen storage container 14 may be of any appropriate size including, but not limited to, a large, stationary storage container or a small, portable storage container. Additionally, oxygen storage container 14 may be adapted to contain different forms of oxygen including, but not limited to, pressurized oxygen gas or liquid oxygen (LOX). Moreover, the oxygen storage container can be replaced by, or augmented with, a home liquid oxygen generating system, which is typically referred to as a liquefaction system. An example of such a system is described in U.S. Pat. No. 5,893,275, the contents of which are incorporated herein by reference.

Oxygen conserving controller 12 is configured with hardware and software appropriate to perform tasks and provide capabilities and functionality as described herein. Oxygen conserving controller 12 is in communication with oxygen regulating valve 10 and nasal cannula 21. Oxygen conserving controller 12 is in communication with an gas flow controller 17, also referred to herein as an oxygen flow switch, that is utilized for setting an appropriate rate of flow of oxygen from the oxygen storage container 14 to the oxygen regulating valve 10. In a preferred embodiment, oxygen flow switch 17 comprises twelve settings for varying the rate of flow of oxygen to the user. Oxygen flow switch 17 is also capable of being set to an "off" position, which prevents a flow of oxygen from reaching an individual through nasal cannula 21.

In an exemplary embodiment, oxygen flow switch 17 is capable of being set to one of five "continuous" flow settings, where each continuous flow setting designates a different rate of oxygen flow. When oxygen flow switch 17 is set to a "continuous" flow setting, oxygen conserving controller 12 provides a constant flow of oxygen directly to nasal cannula 21. In this setting, the oxygen flow effectively bypasses valve 10, or is passed through valve 10 as if it were in the "open" position. The present invention also contemplates setting oxygen flow switch 17 to one of six "conserve" settings, where each conserve setting designates a different rate of oxygen flow. When oxygen flow switch is set to a "conserve" setting, the flow of oxygen controlled based on the monitored parameter, such as the pressure in the nasal cannula, to conserve the amount of oxygen delivered to the user. The present invention further contemplates that each conserve setting corresponds to a different pulse rate of oxygen, where each pulse has a duration of 20 ms to 1000 ms, with a resolution of at least 1 ms. Assuming a flow rate of 12 standard liters per minute (SLPM), the conserve settings allows a pulse rate of oxygen of 4 mL to 200 mL per pulse with a 0.2 mL resolution. For example, the "conserve" settings provide oxygen conservation ratios from 2 to 1 up to 6 to 1, i.e., two to six time more oxygen delivery time than when a continuous flow of oxygen is provided.

When oxygen flow switch 17 is set to the conserve setting, oxygen conserving controller 12 provides oxygen to oxygen regulating valve 10. Oxygen conserving controller 12 triggers oxygen regulating valve 10 between an open and a closed position (pulse) according to a predetermined period of time related to the oxygen flow switch 17 setting. Oxygen flows to nasal cannula 21 when oxygen regulating valve 10 is in the open position, but oxygen does not flow to nasal cannula 21 when oxygen regulating valve 10 is in the closed position. Accordingly, oxygen conserving controller 12 conserves the use of oxygen by only allowing a flow of oxygen to reach the individual through nasal cannula 21 at the appropriate time and appropriate oxygen rate. Oxygen regulating valve 10 includes an oxygen input conduit 33 in communication with oxygen conserving controller 12 to receive a flow of oxygen from oxygen conserving controller 12. Also, oxygen regulating valve 10 includes an oxygen output conduit 35 in communication with oxygen conserving controller 12 and/or nasal cannula 21 for providing a flow of oxygen thereto.

Oxygen regulating valve 10 further includes a valve housing 19 that houses a valve element 24, a bias valve element spring 28, a permanent magnet 23, and a coil 31. Valve housing 19 also includes a valve seat for positioning valve element 24 properly within oxygen regulating valve 10. Valve element 24 comprises an upper portion 25 and a lower portion 26 and is adapted to slide from a first position (e.g., a closed position) to a second position (e.g., an open position). In the closed position, upper portion 25 of valve element 24 engages an opening of oxygen input conduit 33 and, thereby, prevents a flow of oxygen from further entering oxygen regulating valve 10. In other words, upper portion 25 of valve element 24 seals the opening of oxygen input conduit 33 to prevent a flow of oxygen from continuing through oxygen regulating valve 10 and out oxygen output conduit 35. The present invention contemplates providing a sealing gasket or other sealing member to provide a leak free or leak resistant seal over the opening of conduit 33. In the open position, the upper portion of valve element 24 is positioned a distance from the opening of oxygen input conduit 33, thus allowing a flow of oxygen to enter oxygen regulating valve 10 and exit through oxygen output conduit 35 to oxygen conserving controller 12 and/or nasal cannula 21. Lower portion 26 of valve element 24, or a portion of the lower portion of the valve element, is formed from a material that is capable of being attracted by a magnet, such as nickel or iron.

Bias valve element spring 28 is in communication with upper portion 25 of valve element 24. When valve element 24 is in the closed position, bias valve element spring 28 is in an expanded mode and effectively keeps valve element 24 in the closed position, e.g., bias valve element spring 28 is biased to the expanded mode and, therefore, biases valve element 24 in the closed position. When valve element 24 is in the open position, bias valve element spring 28 is in a compressed mode, but constantly attempts to position valve element 24 back to the closed position and, therefore, return to the expanded mode. One skilled in the art will recognize that bias valve element spring 28 may be situated between upper portion 25 of valve element 24 and a portion of housing 19 so that when in the compressed mode, bias valve element spring 28 exerts a force against the portion of housing 19 and upper portion 25 of valve element 24.

A permanent magnet 23 is situated adjacent to lower portion 26 of valve element 24. When valve element 24 is in the closed position, there exists a small spacing, e.g., a gap, between permanent magnet 23 and lower portion 26 of valve element 24. When valve element 24 is in the open position, the lower portion of valve element 24 is positioned next to permanent magnet 23, thus eliminating or nearly eliminating any spacing, e.g., a gap, between valve element 24 and permanent magnet 23. In a preferred embodiment of the present invention, permanent magnet 23 is capable of holding valve element 24 in the open position (even against the biasness of bias valve element spring 28), when lower portion 26 of valve element 24 is in contact with permanent magnet 23. However, permanent magnet 23 is not capable (by itself) to shift valve element 24 from the closed position to the open position. More particularly, the magnetic field produced by permanent magnet 23 alone is not strong enough to create a magnetic linkage with the valve element to overcome the weakening the magnetic linkage that results from increasing the spacing between valve element 24 and permanent magnet 23 when the valve element is in the closed position. In addition or in the alternative, the magnetic field produced by permanent magnet 23 also is not capable of overcoming the biasness of bias valve element spring 28, which attempts to keep valve element 24 in the closed position.

Coil 31 is in communication with permanent magnet 23 and oxygen conserving controller 12. Coil 31 receives a pulse of electric current from oxygen conserving controller 12 through a conductive wiring 29. When coil 31 is provided with a first electric current from oxygen conserving controller 12, coil 31 amplifies the magnetism of permanent magnet 23. Such an amplification of magnetism allows permanent magnet 23 to shift valve element 24 from the closed position to the open position. More specifically, this amplification allows permanent magnet 23 to increase its magnetic field strength to a level sufficient to overcome the spacing between permanent magnet 23 and the lower portion 26 of valve element 24 and/or to overcome the biasness of bias valve element spring 28. In an exemplary embodiment of the present invention, oxygen conserving controller 12 provides a pulse of electric current to coil 31. Accordingly, the magnetism of permanent magnet 23 is only amplified for a short period of time, e.g., for enough time to shift the valve element 24 from the closed position to the open position.

Oxygen conserving controller 12 also provides a second electric current to coil 31. When coil 31 is provided with the second electric current from oxygen conserving controller 12, coil 31 reverses the polarity of permanent magnet 23. The reverse in polarity of permanent magnet 23 repels valve element 24 away from permanent magnet 23, thereby shifting the valve element 24 from the open position to the closed position. In an embodiment of the present invention, oxygen conserving controller 12 provides a pulse of electric current to coil 31. Accordingly, the polarity of permanent magnet 23 is only reversed for a short period of time, e.g., for enough time to shift the valve element 24 from the open position to the closed position.

Figure 2:
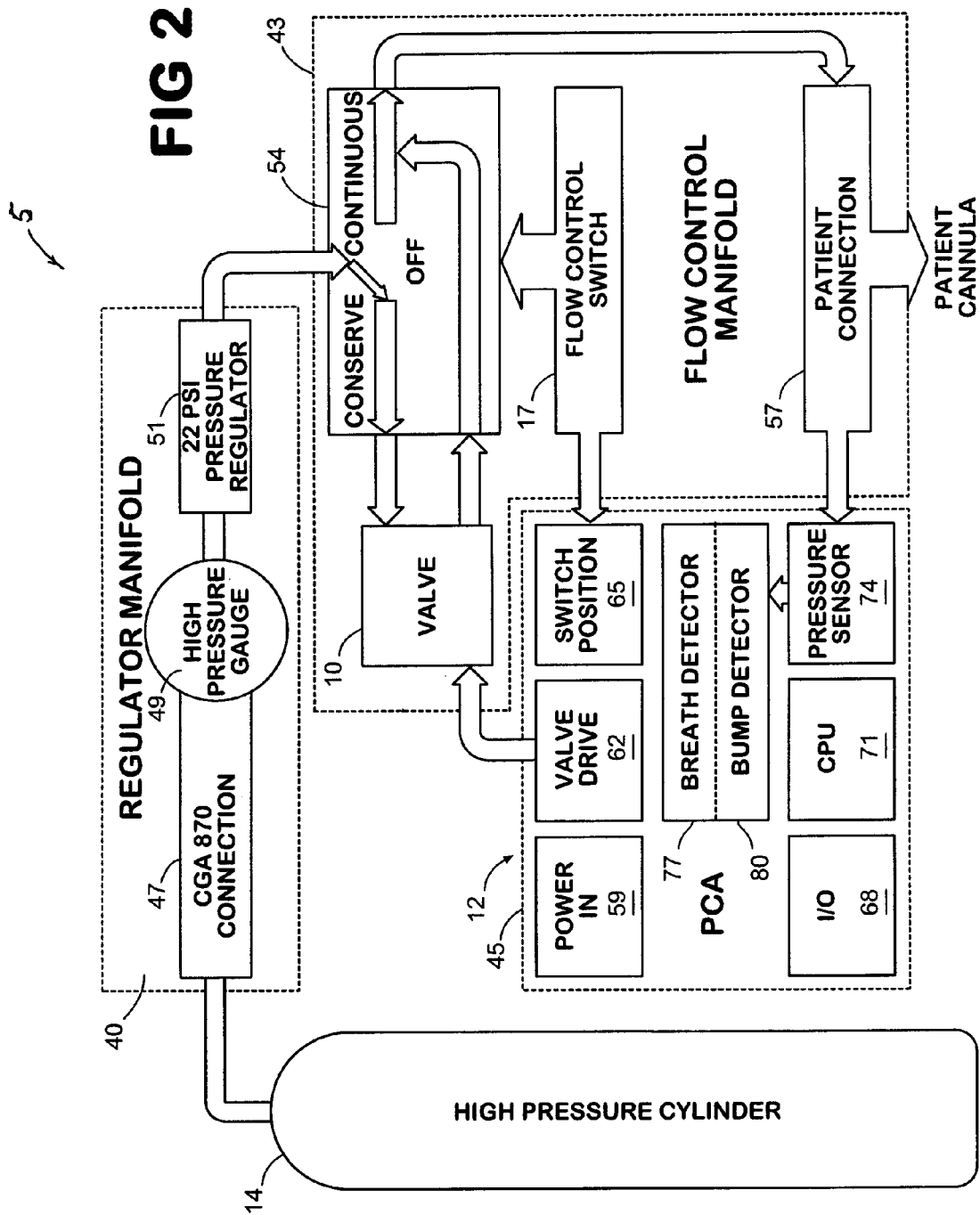
FIG. 2 illustrates a schematic system diagram of the electronic oxygen conserving device of FIG. 1.

As illustrated in FIG. 2, the present invention contemplates that oxygen conserving controller 12 includes a printed circuit assembly (PCA) 45 and a flow control manifold 43, which includes oxygen regulating valve 10. Additionally, oxygen storage container 14 has a regulator manifold 40 that is utilized to discharge oxygen to oxygen conserving controller 12.

In the illustrated exemplary embodiment, regulator manifold 40 includes a Compressed Gas Association (CGA) 870 connection 47, a high pressure gauge 49, and a 22 pounds per square inch (psi) pressure regulator 51. Regulator manifold 40 communicates with oxygen storage container 14 and oxygen conserving controller 12. More particularly, regulator manifold 40 regulates high pressure oxygen from oxygen storage container 14 to a lower internal pressure such as, for example, 22 pounds per square inch gauge (psig). One skilled in the art will recognize that CGA 870 connection 47 is adapted for mating engagement with oxygen storage container 14 (containing high pressure oxygen) and high pressure gauge 49, which provides a display of the current pressure of oxygen within oxygen storage container 14. High pressure gauge 49 also communicates with 22 psi pressure regulator 51. The 22 psi pressure regulator 51 regulates the pressure of the oxygen received from oxygen storage container 14, so that oxygen conserving controller 12 is provided with an appropriate pressure of oxygen, e.g., 22 psi.

PCA 45 is configured with hardware and software appropriate to perform tasks and provide capabilities and functionality as described herein. PCA 45 comprises various components including a power-in unit 59, a valve drive unit 62, a switch position unit 65, an input/output (I/O) unit 68, a central processing unit (CPU) 71, a pressure sensor unit 74, a breath detector unit 77, and a bump detector unit 80. Additionally, flow control manifold 43 is configured with hardware and software appropriate to perform tasks and provide capabilities and functionality as described herein. Flow control manifold 43 includes oxygen regulating valve 10, a patient connection 57, and an oxygen flow switch 17 (also referred to herein as flow control switch 17) having multiple settings 54, such as an off setting, a plurality of continuous flow settings, and a plurality of conserve settings.

CPU 71 generally interfaces with each component of PCA 45 through any conventional technique, such as dedicated hardwired circuits or buses via communication ports on the processor. I/O unit 68 communicates with CPU 71, power-in unit 59, valve drive 62, switch position unit 65, pressure sensor 74, breath detector unit 77, bump detector unit 80, or any combination thereof to provide a communication link between these components and external device. For example, input data is received from an external device I/O unit 68 and then provided to CPU 71 for processing. I/O unit 68 also functions as a conventional I/O terminal, for example providing a display, keypad, mouse, knob, switches, buttons, wireless or hardwired communication link with an external device, or any combination thereof.

Figure 4:
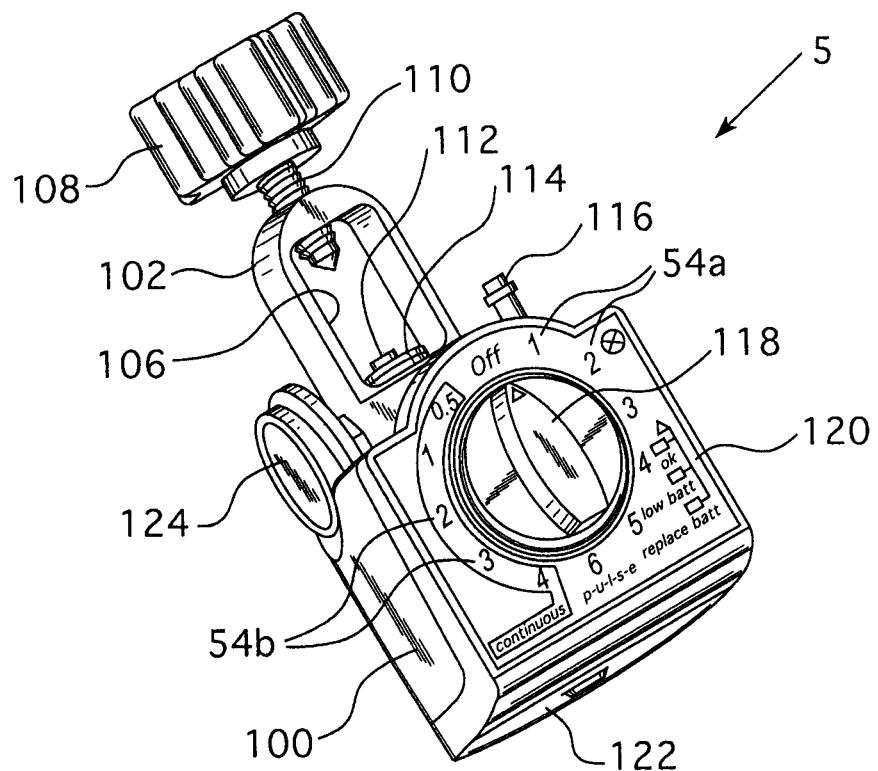
FIG. 4 is a perspective view of an electronic oxygen conserving device according to the principles of the present invention.

Power-in unit 59 provides the components of PCA 45 with an adequate power supply or energy to function properly. Additionally, power-in unit 59 provides an electric current (first and second energy) to valve drive 62 to be provided to oxygen regulating valve 10 for the purpose of triggering oxygen regulating valve 10 to the open or the closed position. The present invention contemplates that power-in unit 59 is any appropriate power source, such as a battery or plurality of batteries. In the illustrated exemplary embodiment, oxygen conserving controller 12 includes individual light emitting diodes (LEDs) that provide an indication when power-in unit 59 has an adequate power supply, a low power supply, and a critical power supply, e.g., needs to be recharged or replaced. Such indicators are illustrated schematically as part of the I/O unit in FIG. 2 and are shown in FIG. 4 as item 120, discussed below. These features, or course, are optional. In addition, other communication techniques, such as an auditory signal or alarm, a vibrating signal or alarm, or any combination thereof can be used to provide information to the user.

As described in more detail below, oxygen conserving controller 12 need only provide one pulse of electric current (a first energy) to trigger oxygen regulating valve 10 from the open position to the closed position and one pulse of electric current (a second energy) to trigger oxygen regulating valve 10 from the closed position to the open position. Requiring only two energy pulses of electric current to open and then close oxygen regulating valve 10 greatly extends the operational life of power-in unit 59.

Valve drive unit 62 is utilized to provide an electric current from power-in unit 59 to oxygen regulating valve 10 for energizing coil 31 switching oxygen regulating valve 10 from a closed position to an open position or vice-versa. Additionally, valve drive unit 62 is adapted to provide the position state (open or closed) of oxygen regulating valve 10 to bump detector unit 80 as described in greater detail below.

Switch position unit 65 is in communication with oxygen flow switch 17 and is utilized for retrieving the switch setting (off, continuous, or conserve) of oxygen flow switch 17. Accordingly, switch position unit 65 is adapted to provide the switch setting of oxygen flow switch 17 to CPU 71.

Pressure sensor unit 74 is utilized to sense the pressure exerted on nasal cannula 21. Pressure sensor unit 74 communicates with nasal cannula 21 through patient connection 57. As an individual breathes in, pressure sensor unit 74 detects a negative pressure through nasal cannula 21 or a drop in pressure. Similarly, as an individual breathes out, pressure sensor unit 74 detects a positive pressure through nasal cannula 21 or an increase in pressure. Pressure sensor unit 74 is further adapted to provide breath detector unit 77 with a signal indicating (or that can be used to determine) whether the pressure sensor unit has detected a positive or negative pressure from nasal cannula 21 or a has detected a pressure increase or a pressure decrease.

Breath detector unit 77 is utilized to determine whether an individual is breathing in or out based on the signal received from pressure sensor unit 74. If breath detector unit 77 determines that an individual is breathing in through nasal cannula 21, then breath detector unit 77 signals to CPU 71 that oxygen regulating valve 10 should be open. Likewise, if breath detector unit 77 determines that an individual is breathing out through nasal cannula 21, then breath detector unit 77 signals to CPU 71 that oxygen regulating valve 10 should be closed.

Bump detector unit 80 is utilized to determine whether oxygen regulating valve 10 has been accidentally bumped to an inappropriate position, e.g., the oxygen regulating valve 10 is open when it should be closed or vice versa. Bump detector unit 80 receives the position state of oxygen regulating valve 10 from valve drive unit 62 and receives the breathing state of the individual from breath detector unit 77.

Based on the position state of oxygen regulating valve 10 and the breathing state of the individual, bump detector unit 80 determines whether oxygen regulating valve 10 is in the correct position state. If bump detector unit 80 determines that oxygen regulating valve 10 is not in the correct position state, then bump detector unit 80 signals to CPU 71 that valve drive unit 62 needs to send an electric current to oxygen regulating valve 10 to change the current position state to the correct position state.

In another embodiment of the present invention, bump detector unit 80 is adapted to measure the acceleration of oxygen conserving controller 12. If a predetermined acceleration, e.g., force, has been exceeded, then bump detector unit 80 determines that oxygen regulating valve 10 has shifted to the incorrect position state and, therefore, bump detector unit 80 signals CPU 71 to correct the position state of oxygen regulating valve 10.

In yet another embodiment of the present invention, bump detector unit 80 senses the actual flow of oxygen to nasal cannula 21. If a flow of oxygen is detected when oxygen regulating valve 10 should be closed, then bump detector unit 80 determines that oxygen regulating valve 10 has shifted to the incorrect position state. Further, if bump detector unit 80 detects a flow of oxygen of a predetermined amount and determines that oxygen regulating valve 10 is in the closed state, then bump detector unit 80 signals to CPU 71 that a leak exists within oxygen conserving controller 12. One skilled in the art will recognize that the individual may be notified of an oxygen leak in a variety of ways including, but not limited to, an audible alarm, a leak alert light or LED, or through any other appropriate display.

In still a further embodiment of the present invention, bump detector unit 80 senses the generated electric current produced when valve element 24 moves relative to biased valve element spring 28. If biased valve element spring 28 was not in a compressed state and valve element 24 was bumped to the open position, then a small electric current is produced by the movement of valve element 24. When bump detector unit 80 senses the generated electric current, bump detector unit 80 signals CPU 71 to correct the position state of oxygen regulating valve 10.

In still a further embodiment of the present invention, valve drive unit 62 does not determine whether oxygen regulating valve 10 is in an open or closed position. When bump detector unit 80 receives a pressure reading from pressure sensor unit 74, bump detector unit 80 determines whether a positive pressure (or increasing pressure) or a negative pressure (or decreasing pressure) has been detected. If a positive pressure has been detected, then bump detector unit 80 assumes that oxygen regulating valve 10 is open. In which case, bump detector unit 80 signals CPU 71 to correct the position state of oxygen regulating valve 10.

In operation, switch position unit 65 determines the oxygen flow setting of oxygen flow switch 17 and provides the selected oxygen flow setting to CPU 71 via I/O unit 68. If oxygen flow switch 17 is in the off setting or any of the continuous flow settings, CPU 71 remains idle as the appropriate flow of oxygen, if any, is provided directly from oxygen storage container 14 to nasal cannula 21 via patient connection 57. If, however, oxygen flow switch 17 is in any of the conserve settings, CPU 71 initiates management of oxygen regulating valve 10 as the appropriate flow of oxygen is provided directly from oxygen storage container 14 to oxygen regulating valve 10.

Generally, oxygen regulating valve 10 is biased (and initialized) to the closed position. Pressure sensor unit 74 senses (1) a positive or increasing pressure, or (2) a negative or decreasing pressure from nasal cannula 21, and provides a signal to breath detector unit 77 indicating the type of pressure or pressure change detected. If breath detector unit 77 receives a signal from pressure sensor unit 74 that a negative pressure or decreasing pressure has been detected in nasal cannula 21, then breath detector unit 77 provides a signal to CPU 71 indicating that oxygen regulating valve 10 should be opened. Otherwise, if breath detector unit 77 receives a signal from pressure sensor unit 74 that a positive pressure or increasing has been detected in nasal cannula 21, then breath detector unit 77 provides a signal to CPU 71 indicating that oxygen regulating valve 10 should be closed.

Upon receiving a signal from breath detector unit 77, CPU 71 provides a signal to valve drive unit 62 that oxygen regulating valve 10 should be switched to the open or closed position, as the case may be. Valve drive unit 62 then provides an electric current from power-in unit 59 to oxygen regulating valve 10. As described above, coil 31 either amplifies the magnetism of permanent magnet 23 to attract (and shift) valve element 24 to the open position, or reverses the polarity of permanent magnet 23 to repel (and shift) valve element 24 to the closed position. For example, the present invention contemplates that valve drive unit 62 provides an electric current of 250 milliwatts (mW) for approximately 5 milliseconds (ms). By providing only two pulses of electric current for opening and closing oxygen regulating valve 10, power-in unit 59 is capable being utilized for an extended period of time before having to be recharged or replaced.

The low power requirements of the system is extremely advantageous. Conventional electronic oxygen conserving systems have a deficiency in that they may be unreliable or have a relatively short operating period due to battery drainage. By having an electronic pulse being presented to the valve only in order to move the valve between open and closed positions, versus manipulating the valve via a constant supply of current, the control system in the oxygen conserver of the present invention is operable over an extremely long period time or over an extremely large number of breaths. For instance, tests have shown that when utilized for an assumed rate of four hours of patient use per day, and 30 breaths per minute, the battery life of four AA Duracell batteries MN1500 each 1.5 volts or equivalent lasted for two years via accelerated testing. The system provides over 3,500,000 breaths at an energy consumption of 5.85E-6 watt-seconds of power per breath or per dose. This durational reliability of the system is critical for commercial acceptance.

As the individual breathes in and out through nasal cannula 21, pressure sensor unit 74 continues to signal breath detector unit 77 with the status of the pressure on nasal cannula 74. Breath detector unit 77, therefore, continues to signal CPU 71 that a change in pressure has occurred and, accordingly, CPU 71 continues to signal valve drive unit 62 to shift the position state of oxygen regulating valve 10.

Simultaneously, bump detector unit 80 is receiving a signal from pressure sensor unit 74 with the status of the pressure on nasal cannula 74 and a signal from valve drive unit 62 as to the position state of oxygen regulating valve 10. If bump detector unit 80 determines that oxygen regulating valve 10 is open when it should be closed or is closed when it should be open, then bump detector unit 80 signals CPU 71 that oxygen regulating valve is in the wrong position state. Upon receiving the signal from bump detector unit 80, CPU 71 provides a signal to valve drive unit 62 to shift the position state of oxygen regulating valve 10 to the correct position state, e.g., closed or open.

In an alternative embodiment of the present invention, CPU 71 utilizes a timer to determine how long to keep oxygen regulating valve 10 in the open and closed position. The length of time to keep oxygen regulating valve 10 in the open and closed position may be determined by the oxygen flow setting of oxygen flow switch 17. As described above, oxygen flow switch 17 comprises six conserve settings to provide different oxygen flow rates to nasal cannula 21. Each conserve setting may be associated with a predetermined time period to be used by CPU 71 in determining how long to keep oxygen regulating valve 10 in the open and closed position. Instead of examining the signal from pressure sensor unit 74, bump detector unit 80 need only determine whether oxygen regulating valve 10 is in the correct position state during the appropriate time period.

Because oxygen conserving device 5 is typically associated with portable devices, oxygen regulating valve 10 may be subjected to varying degrees of inside and outside temperatures. Additionally, oxygen conserving device 5 is likely to be turned on and off by the individual as the need for oxygen changes. Such temperature changes and intermittent use could result in valve element 24 becoming stuck in a position state within oxygen regulating valve 10. When stuck in a position state within oxygen regulating valve 10, valve element 24 may not reliably shift when a normal electric current is provided to Coil 31. A stuck valve element 24 could lead to oxygen regulating valve 10 not being open during and individual's first breath after initial power-up of oxygen conserving device 5.

In an exemplary embodiment of the present invention, CPU 71 determines whether oxygen conserving controller 12 has just been initialized. If CPU 71 determines that oxygen conserving controller 12 has just been initialized, then CPU 71 provides a signal to valve drive unit 62 indicating that an extended electric current should be provided to oxygen regulating valve 10. Valve drive unit 62 provides the extended electric current, e.g., a 20 ms pulse instead of a standard 5 ms pulse, to oxygen regulating valve 10 to ensure that valve element 24 shifts position states, thus preventing the oxygen regulating valve 10 from remaining stuck in a particular position state. After valve element 24 is shifted to a different position state, valve drive unit 62 provides regular electric current, e.g., 5 ms pulse instead of a 20 ms pulse, to oxygen regulating valve 10.

Figure 3:
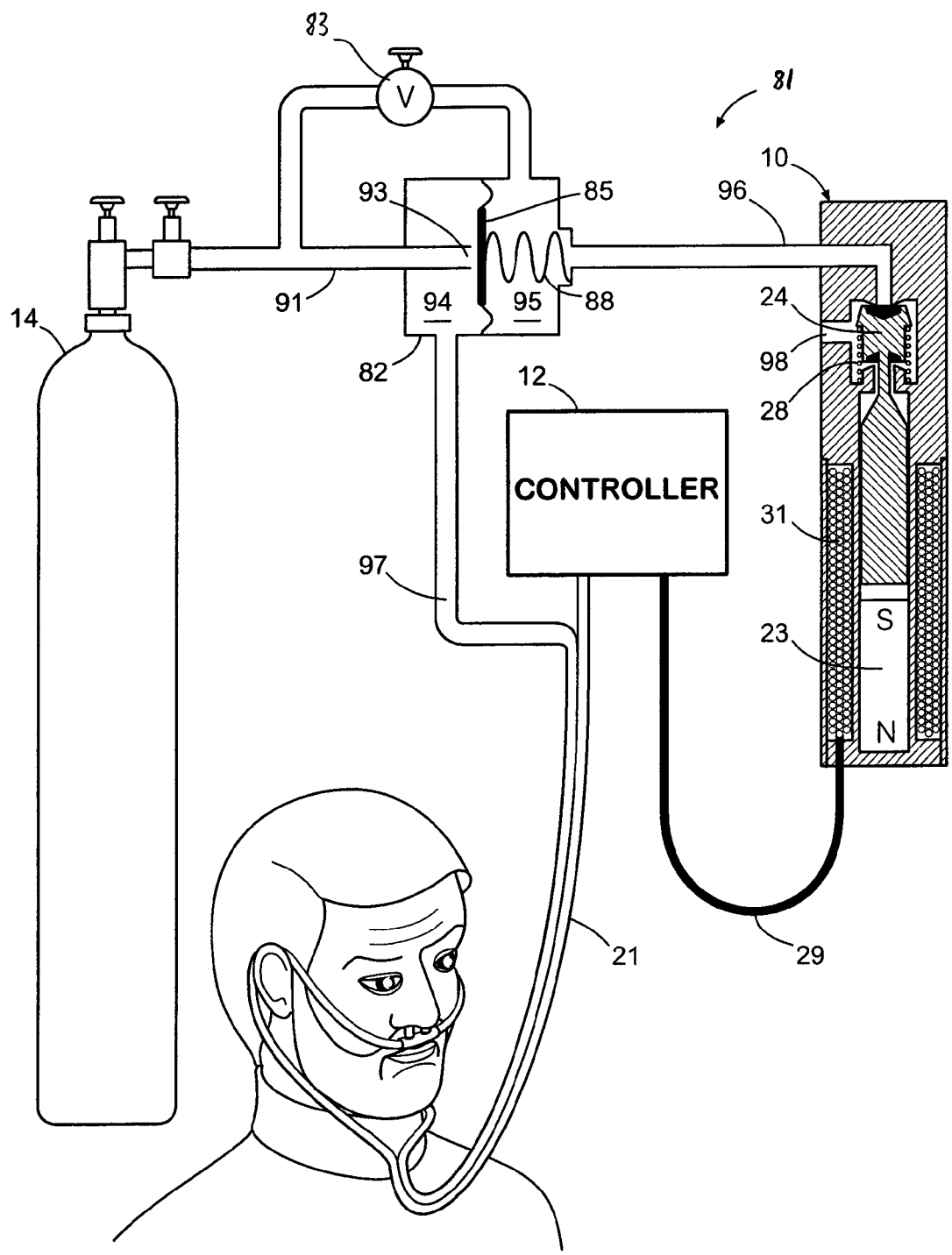
FIG. 3 illustrates an electronic controller for a pneumatic oxygen conserving device according to the principles of the invention.

FIG. 3 illustrates an electronic controller for a pneumatic oxygen conserving device 80 according to a second embodiment of the present invention. Pneumatic oxygen conserving device 80 is intended for use by an individual who receives supplemental oxygen from an oxygen storage container. Pneumatic oxygen conserving device 80 includes an oxygen delivery chamber 82 that contains a slave valve described in detail below, an oxygen conserving controller 12, and an oxygen regulating valve 10 that contains a primary valve that controls the operation of the slave valve. In operation, oxygen storage container 14 provides a flow of oxygen to oxygen delivery chamber 82 and simultaneously to a bypass valve 83. The simultaneous flow of oxygen generally equalizes the pressure within the oxygen delivery chamber 82 one either side of a diaphragm 85 enabling a spring 88 to bias the diaphragm in a closed position over an oxygen input conduit opening 93, preventing oxygen from flowing to the patient. In order for oxygen to flow to the patient, the diaphragm must move away from oxygen input conduit opening 93. This is accomplished by venting off the bypass oxygen to the ambient environment, thereby releasing the pressure in chamber 95 behind the diaphragm enabling oxygen to flow from the oxygen storage container through nasal cannula 21 to the patient.

Oxygen delivery chamber 82 is in communication with oxygen storage container 14 through an oxygen delivery input conduit 91 and with oxygen regulating valve 10 through a pressure release input conduit 96. Oxygen delivery chamber 82 comprises a first chamber 94 that permits flow of oxygen from oxygen storage container 14 via oxygen delivery input conduit 91 to enter an oxygen delivery output conduit 97. Oxygen delivery chamber 82 further comprises an oxygen delivery diaphragm 85 and an oxygen delivery bias spring 88. When the oxygen flowing through the bypass valve generates pressure within a second chamber 95 greater than or equal to the pressure within a first chamber 94, oxygen delivery bias spring 88 positions oxygen delivery diaphragm 85 in a first position sealing off communication from oxygen delivery input conduit 91 with oxygen delivery output conduit.

For oxygen to be supplied to the patient, the pressure within second chamber 95 must be reduced such that the pressure from the oxygen flowing through oxygen delivery input conduit 91 is greater thereby pushing diaphragm 85 away enabling oxygen to flow to the patient. Release of pressure from second chamber 95 is accomplished by pneumatic oxygen conserving device 80.

Pneumatic oxygen conserving device 80 includes oxygen conserving controller 12 and oxygen regulating valve 10 as described above with reference to FIGS. 1 and 2. Oxygen regulating valve 10 is in communication with second chamber 95 via a pressure release input conduit 96. Typically, valve element 24 is biased to the closed position and, therefore, does not allow pressure to be released from second chamber 95 and pressure release input conduit 96. When oxygen conserving controller 12 detects that the individual has breathed in through nasal cannula 21, e.g., pressure sensor unit 74 detects a negative pressure (or a decrease in pressure) in nasal cannula 21, oxygen conserving controller 12 triggers oxygen regulating valve 10 to the open position, e.g., valve drive unit 62 provides an electric current to coil 31 to amplify the magnetism of permanent magnet 23, thus shifting valve element 24 to the open position, enabling the oxygen contained within chamber 95 to vent to the ambient atmosphere via an exhaust port 98. When oxygen conserving controller 12 detects that the individual has breathed out through nasal cannula 21, e.g., pressure sensor unit 74 detects a positive pressure (or an increase in pressure) in nasal cannula 21, oxygen conserving controller 12 triggers oxygen regulating valve 10 to the closed position, e.g., valve drive unit 62 provides an electric current coil 31 to reverse polarity of permanent magnet 23, thus shifting valve element 24 to the closed position. This enables the oxygen pressure to build back up in second chamber 95, resulting in the closing of opening 93 of oxygen delivery input conduit 91 by diaphragm 85.

Oxygen conserving controller 12 and oxygen regulating valve 10 assist in the release of pressure within second chamber 95, so that an individual that does not create a significant negative pressure when breathing in through nasal cannula 21 can still use pneumatic oxygen conserving device 80. Other features of oxygen conserving controller 12 and oxygen regulating valve 10, as described above, may also be utilized in this embodiment of the present invention.

Figure 5:
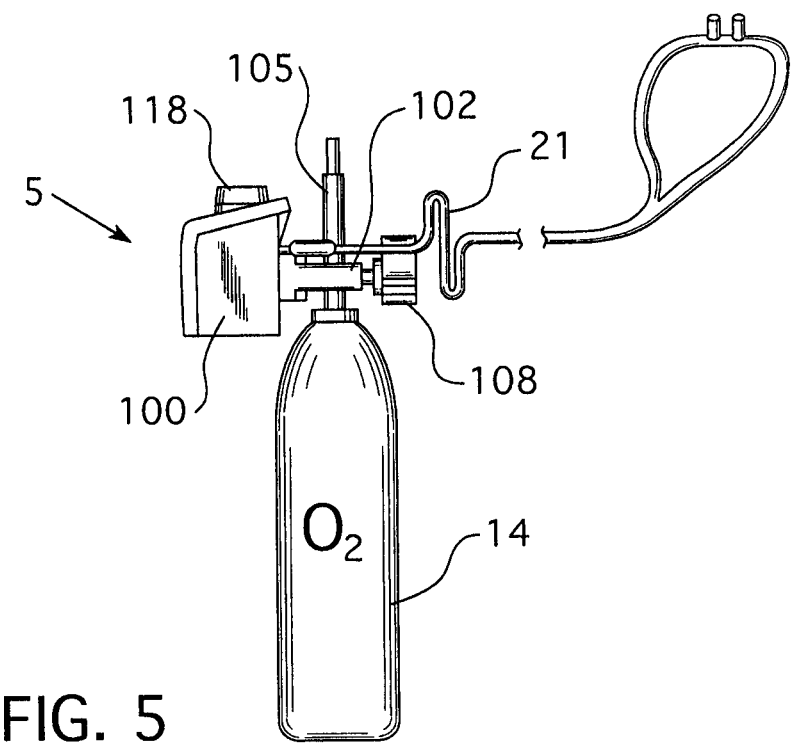
FIG. 5 is a side view illustrating the attachment of the electronic oxygen conserving device of FIG. 4 to an oxygen storage container.

FIG. 4 is a perspective view of an exemplary embodiment electronic oxygen conserving device 5 according to the principles of the present invention, and FIG. 5 illustrates the electronic oxygen conserving device attached to an oxygen storage container 14. Conserving device 5 including a housing 100 that contains the flow control manifold and the printed circuit board discussed above. A mounting stem 102 protrudes from the housing. An outlet stem 104 of a storage tank 14 inserts into an opening 106 defined in mounting stem 102. A knob 108 us used to tighten an attachment screw 110 such that the attachment screw secures the conserving device onto the stem of the storage tank.

The stem of the storage tank includes a discharge port (not shown) that must be aligned with an inlet port 112 so that gas from the storage tank enters electronic oxygen conserving device 5 through the inlet port. A high pressure seal 114 is provided at inlet port 112 to ensure a leak resistant seal is maintained with the storage tank. It can be appreciated that inlet port 112 corresponds to an inlet to oxygen flow control switch 17 in FIG. 1. Although not shown, the present invention contemplates that mounting pins or other alignment mechanisms can be provided on the conserver to ensure that the mounting stem is properly positioned on the outlet stem of the oxygen storage tank.

In the illustrated exemplary embodiment, electronic oxygen conserving device 5 includes a rotary selector knob 118 that functions as oxygen flow switch 17 discussed above. FIG. 4 shows knob 118 set to the "off" position. Moving knob 118 clockwise, the user is provided with a plurality of "conserve" or "pulse" settings 54a, e.g., settings 1, 2, 3, 4, 5, or 6. In the present embodiment, the following pulse dose volumes are associated with each setting:

| Setting | Pulse Dose Volume (cc) |
| --- | --- |
| 1 | 12.0 |
| 2 | 24.0 |
| 3 | 36.0 |
| 4 | 48.0 |
| 5 | 64.0 |
| 6 | 72.0 |

Moving knob 118 counterclockwise, the user is provided with a plurality of "continuous" settings 54b, e.g., settings 0.5, 1, 2, 3, and 4.

A plurality of LEDs 120 are provided on the face of housing 100 that function as I/O device 68 discussed above. For example, the present invention contemplates that LEDs 120 indicate the battery life of the unit, such as "OK", "low", or "replace". The present invention also contemplates flashing an LED each time a dose of oxygen is delivered to that the user can clearly tell whether the device is functioning. A battery access panel 122 is provided on another face of the housing, and a pressure or oxygen content gage 124 is provided to show the pressure of the gas entering the conserver or the amount of gas remaining in the storage canister. Cannula 21 attaches to a canula fitting 116.

It can be appreciated that an advantage of the present invention is that the energy required to control the oxygen conserving device is only used to provide a single pulse to open the valve and a single pulse to close the valve. No electrical energy is required to maintain the valve in either an open or closed state. Consequently, a electrically powered oxygen conserving device with an electronic valve is provided where the power required to deliver a single oxygen pulse is independent of the time the valve is held open. Likewise, the power required to deliver a single oxygen pulse is independent of the volume of oxygen in each pulse. Also, the power required to deliver a single oxygen pulse is independent of the patient selected flow setting, i.e., 1, 2, 3, 4, 5, or 6, of the variable oxygen flow switch wherein more oxygen is provided depending on the flow setting.

The oxygen conserving device is intended as a pulse dose delivery device for medical-grade oxygen from portable high-pressure oxygen cylinders. The oxygen conserving device extends the use time from a supply of oxygen. As opposed to continuous delivery of oxygen, the oxygen conserving device delivers oxygen only when needed by the patient. The oxygen conserving device generally has a conservation ratio between 2:1 and 6:1. Implementation of the invention enables different pulse volumes of oxygen to be delivered to the patient utilizing the same amount of power from the energy source. For instance, for the preferred embodiment, the power required to regulate the valve element can be calculated as follows:

$$(4.5 \text{ VDC} \times 0.090 \text{ AMP} \times 0.005 \text{ sec}) + (4.5 \text{ VDC} \times 0.090 \text{ AMP} \times 0.005 \text{ sec}) = 4.05\text{E-}03 \text{ watt-seconds.}$$

Thus, the power used by the oxygen conserving device to deliver a dose or pulse of gas, where typically one dose or pulse is delivered during each breath, 4.05E-03 watt-seconds. To deliver twelve milliliters of oxygen, which corresponds to a conservation setting of 1, or to deliver seventy-two milliliters of oxygen, which corresponds to a conservation setting of 6, the oxygen conserving device uses 4.05E-03 watt-seconds of power, because the power required to open and close the valve element does not change based on how long the valve element remains open. Thus, the power consumption of the present gas conserver is independent of the volume of gas delivered to the user during a single breath or pulse/dose cycle, the time that the valve is open during the single breath or pulse/dose cycle, or the flow setting selected by the patient.

It can be appreciated that the power to deliver a certain volume of gas can be determined by dividing the power to open and close the valve element, i.e., 4.05E-03 watt-seconds, by the volume of gas delivered during the interval that the valve element was in the open position. The various ratios of power versus milliliter of oxygen delivered by the gas conserving device on the present invention are as follows: (a) 3.375E-04 for twelve milliliters, which is the amount of oxygen delivered at a conservation setting of 1; (b) 1.675E-04 for twenty-four milliliters, which is the amount of oxygen delivered at a conservation setting of 2; (c) 1.125E-04 for thirty-six milliliters, which is the amount of oxygen delivered at a conservation setting of 3; (d) 8.4375E-05 for forty-eight milliliters, which is the amount of oxygen delivered at a conservation setting of 4; (e) 6.75E-05 for sixty milliliters, which is the amount of oxygen delivered at a conservation setting of 5; and (f) 5.625E-05 for seventy-two milliliters which is the amount of oxygen delivered at a conservation setting of 6.

It can be further appreciated that the oxygen conserving device is most efficient, i.e., provides a high volume of gas during a single breath or pulse dose, at a lower power consumption when the gas flow switch is at a conservation setting of 6, so that seventy-two milliliters of gas are delivered during each breath or pulse dose. In other words, at the twelve milliliter setting, the oxygen conserving device uses 3.375E-04 watt-seconds of power to deliver each milliliter of oxygen. This power usage per milliliter of gas delivered gets smaller as the amount of gas delivered during each dose is increased because more oxygen is being delivered but the power required to deliver that amount of oxygen, i.e., the power to open and close the valve element, remains substantially unchanged.

In the embodiments described above, when the oxygen conserving device is operating in the "conserve" setting, a pulse or dose of gas delivered during each breath. It is to be understood, that the present invention also contemplates delivering the dose of gas at other intervals, such as at every other breath, every third breath, every forth breath, an so on. The present invention also contemplates that the actual start of gas delivery need not take place upon detection of inspiration, but can be started slightly before the user being to inhale, for example. Likewise, the termination of gas delivery need not take place at the transition from inspiration to expiration, but can take place prior to the end of the inspiratory cycle.

In addition, the present invention contemplates using any conventional technique for detecting transitions between inspiration and expiration, in addition to or in place of the pressure sensing technique noted above. For example, the present invention contemplates monitoring flow, temperature, sound, muscle effort, neural activity, or any other physiological characteristic indicative of transitions between inspiration and expiration using any conventional sensing device. An effort belt worn about the chest, for example, can be used to detect respiratory activity.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A gas conserving device comprising:
a gas flow switch having a plurality of selectable settings, wherein a different quantity of gas is delivered to a patient by the gas conserving device for each setting in the plurality of selectable settings;
a valve housing adapted to be disposed between a gas source and a patient, wherein the valve housing includes a valve body and a valve seat disposed in the valve body;
a valve element disposed within the valve body, wherein a portion of the valve element is adapted to seat against the valve seat responsive to the valve element being in a closed position, and wherein the portion of the valve element is spaced apart from the seat responsive to the valve element being in an open position;
a resilient member configured to bias the valve element toward the closed position; and
a permanent magnet configured to magnetically attract the valve element toward the open position, and hold the valve element in the open position without electrical energy or residual magnetism caused by the electrical energy,
wherein, with the valve in the closed position, the bias provided by the resilient member is stronger than the magnetic attraction between the permanent magnet and the valve element to maintain the valve element in the closed position, and with the valve in the open position magnetic attraction between the permanent magnet and the valve element is stronger than the bias provided by the resilient member to the valve element to hold the valve element in the open position; and an electrical energy source adapted to move the valve element between the closed position and the open position, wherein the energy source provides substantially a same amount of energy to move the valve element independent of the setting of the gas flow switch.

2. The gas conserving device of claim 1, having a conservation ratio over a range from 2:1 to 6:1.

3. A gas conserving device comprising:
a valve housing adapted to be disposed between a gas source and a patient, wherein the valve housing includes a valve body and a valve seat disposed in the valve body;
a valve element disposed within the valve body, wherein a portion of the valve element is adapted to seat against the valve seat responsive to the valve element being in a closed position thereby substantially disabling a flow of gas to the patient, and wherein the portion of the valve element is spaced apart from the seat responsive to the valve element being in an open position thereby enabling the flow of gas to the patient;
a resilient member configured to bias the valve element toward the closed position; and
a permanent magnet configured to magnetically attract the valve element toward the open position, and hold the valve element in the open position without electrical energy or residual magnetism caused by the electrical energy,
wherein, with the valve in the closed position, the bias provided by the resilient member is stronger than the magnetic attraction between the permanent magnet and the valve element to maintain the valve element in the closed position, and with the valve in the open position magnetic attraction between the permanent magnet and the valve element is stronger than the bias provided by the resilient member to the valve element to hold the valve element in the open position; and
an electrical energy source adapted to move the valve element between the closed position and the open position, the energy source providing a substantially same amount of energy to the valve element independent of an amount of time the valve element remains in the open position.

4. The gas conserving device of claim 3, having a conservation ratio over a range from 2:1 to 6:1.

5. A gas conserving device comprising:
a valve system having a valve element adapted to provide a predetermined quantity of gas to a patient by moving the valve element between a closed position and an open position;
a resilient member configured to bias the valve element toward the closed position; and
a permanent magnet configured to magnetically attract the valve element toward the open position, and hold the valve element in the open position without electrical energy or residual magnetism caused by the electrical energy,
wherein, with the valve in the closed position, the bias provided by the resilient member is stronger than the magnetic attraction between the permanent magnet and the valve element to maintain the valve element in the closed position, and with the valve in the open position magnetic attraction between the permanent magnet and the valve element is stronger than the bias provided by the resilient member to the valve element to hold the valve element in the open position; and
an electrical energy source adapted to provide energy to the valve system to move the valve element between the closed position and the open position, wherein the energy source provides a total of 4.05E-03 watts-seconds or less to the valve system to permit a quantity of oxygen to be delivered of at least twelve milliliters.

6. The gas conserving device of claim 5, having a conservation ratio over a range from 2:1 to 6:1.

7. A gas conserving device comprising:
a valve system having a valve element adapted to provide a predetermined quantity of gas to a patient by moving the valve element between a closed position and an open position;
a resilient member configured to bias the valve element toward the closed position; and
a permanent magnet configured to magnetically attract the valve element toward the open position, and hold the valve element in the open position without electrical energy or residual magnetism caused by the electrical energy,
wherein, with the valve in the closed position, the bias provided by the resilient member is stronger than the magnetic attraction between the permanent magnet and the valve element to maintain the valve element in the closed position, and with the valve in the open position magnetic attraction between the permanent magnet and the valve element is stronger than the bias provided by the resilient member to the valve element to hold the valve element in the open position; and
an electrical energy source adapted to provide energy to the valve system to move the valve element between the closed position and the open position such that the valve system remains in the open position for a predetermined period of time and such that a ratio of watts-seconds per milliliter of gas delivered is less than or equal to 3.375E-04.

8. The gas conserving device of claim 7, having a conservation ratio over a range from 2:1 to 6:1.

* * * * *